United States Patent [19]

Cusic et al.

[11] 3,997,572

[45] Dec. 14, 1976

[54] N-[2-(NITRO-1-IMIDAZOLYL)ETHYL]-NAPHTHAL IMIDES

[75] Inventors: John W. Cusic, Skokie; Ernest F. Levon, Evanston, both of Ill.

[73] Assignee: G. D. Searle & Co., Chicago, Ill.

[22] Filed: Aug. 4, 1975

[21] Appl. No.: 601,375

Related U.S. Application Data

[63] Continuation-in-part of Ser. No. 383,911, July 30, 1973, Pat. No. 3,917,636, which is a continuation-in-part of Ser. No. 110,665, Jan. 28, 1971, Pat. No. 3,770,763, which is a continuation-in-part of Ser. No. 796,225, Feb. 3, 1969, Pat. No. 3,642,836.

[52] U.S. Cl. ............... 260/281 NH; 260/281 GN; 260/295.5 B; 424/258

[51] Int. Cl.$^2$ .................................. C07D 401/06

[58] Field of Search .......................... 260/281 NH

[56] References Cited

UNITED STATES PATENTS 3,625,947  12/1971  Noguchi ............... 260/281 NH

*Primary Examiner*—Alton D. Rollins
*Assistant Examiner*—Mark L. Berch
*Attorney, Agent, or Firm*—John J. Kolano

[57] ABSTRACT

Imides having a nitroimidazolylethyl group as a N-substituent are described herein. They are anti-bacterial and anti-protozoal agents. The compounds are prepared by the reaction of the appropriate imide with the chloroethylimidazole or with the tosylate or mesylate of the corresponding hydroxyethyl compound.

1 Claim, No Drawings

N-[2-(NITRO-1-IMIDAZOLYL)ETHYL]NAPHTHAL IMIDES

The present application is a continuation-in-part of application Ser. No. 383,911, now U.S. Pat. No. 3,917,636 filed July 30, 1973 which in turn is a continuation-in-part of application Ser. No. 110,665, filed Jan. 28, 1971 now U.S. Pat. No. 3,770,763 and that in turn is a continuation-in-part of application Ser. No. 796,225, filed Feb. 3, 1969, now U.S. Pat. No. 3,642,836.

The present invention relates to a group of N-substituted imides. In particular, it relates to a group of compounds having the following general formula

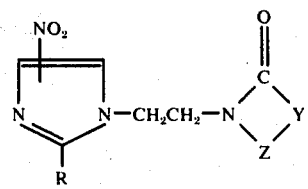

wherein R is selected from the group consisting of hydrogen and lower alkyl; Y is selected from the group consisting of alkylene, alkenylene, cycloalkylene, cycloalkenylene and arylene and

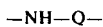

wherein Q is selected from the group consisting of phenylene, cycloalkylidene, adamantylidene and

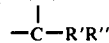

wherein R' and R'' are each selected from the group consisting of lower alkyl and phenyl; and Z is selected from the group consisting of carbonyl and sulfonyl. When Z is carbonyl, an imide structure results.

The nitro group as depicted in the preceding structural formula can be in the 4- or 5-position of the imidazole ring.

The alkylene and alkenylene radicals referred to above contain from 2 to 5 carbon atoms. In these radicals, at least two carbon atoms separate the free valences. Preferably, 2 to 3 carbon atoms separate the free valences so that when the radicals are combined with the imide structure, for example, a 5- or 6-membered ring results. Some examples of alkylene and alkenylene groups are ethylene, trimethylene, and vinylene. Thus, when Z is carbonyl and Y is each of the aforementioned groups, the imides involved are succinimide, glutarimide, and maleimide, respectively. The indicated imides can further contain one or more alkyl substituents to give structures such as 2-methylsuccinimide and 3,3-dimethylglutarimide. The alkyl substituents can further be combined to give a spiro imide structure. An example of this type of structure is 1,1-cyclohexanediacetimide.

The cycloalkylene and cycloalkenylene radicals preferably contain 5 to 7 carbon atoms in the ring with the free valences on adjacent carbon atoms. Examples of such groups are 1,2-cyclohexylene and 4,5-cyclohex-1-enylene.

When Y is arylene, radicals having two free aromatic valences are involved. Examples of Y thus are phenylene and naphthylene. Examples of imides involved are phthalimide, naphthalimide, 1,2-naphthalenedicarboximide, and 2,3-naphthalenedicarboximide. The benzene and naphthalene rings in the aforementioned imides can further be substituted with one or more alkyl groups such as methyl, with one or more halogen atoms such as chlorine, or with nitro. Y can further represent pyridinediyl so that derivatives of quinolinimide are involved. When Y in the above structure is phenylene, Z can also be sulfonyl to give derivatives of o-sulfobenzimide.

When Y in the above formula is

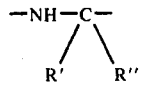

and Z is carbonyl, then

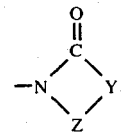

is a 5,5-disubstituted hydantoin. Preferred R' and R'' substituents are lower alkyl radicals containing up to six carbon atoms and phenyl. Examples of such lower alkyl radicals are methyl, ethyl and propyl. Examples of substituted hydantoins are 5,5-dimethylhydantoin, 5,5-diethylhydantoin, and 5,5-diphenylhydantoin. When R' and R'' are combined, =CR'R'' is a cycloalkylidene group and spirohydantoins are involved. The cycloalkylidene groups preferably contain 5 to 7 carbon atoms in the ring and can be exemplified by cycloheptylidene. A more complex ring structure is also possible, such as when =CR'R'' is adamantylidene.

The compounds of the present invention are conveniently prepared from a substituted imidazole of the following formula

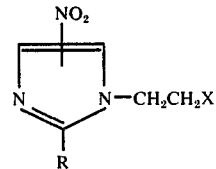

wherein X is chlorine, methanesulfonyloxy or toluenesulfonyloxy. This compound is reacted with an alkali metal salt, preferably the sodium or potassium salt, of the appropriate imide to give the compounds of the present invention. Where X in the above formula is methanesulfonyloxy or toluenesulfonyloxy, the necessary starting materials can be prepared by contacting the appropriate hydroxyethylimidazole with methanesulfonyl chloride or toluenesulfonyl chloride.

Where the compounds of the present invention are imides of dicarboxylic acids, they can be hydrolyzed with base to effect partial opening of the imide structure and give the corresponding amide-carboxylic acid.

The compounds of the present invention are useful because of their anti-biotic activity against a number of organisms. Thus, they inhibit the growth of protozoa such as *Tritrichomonas foetus* and *Trichomonas vaginalis* and they inhibit the growth of bacteria such as *Diplococcus pneumoniae* and *Bacillus subtilis*. The present compounds are also anthelmintic agents as demonstrated by their activity against *Syphacia obvelata* in rats infested with this nematode.

Evidence of the anti-protozoal utility of the present compounds is provided by standardized tests for their capacity to inhibit the growth of *Tritrichomonas foetus* and *Trichomonas vaginalis* which are carried out in the following manner. A modified Diamond medium is prepared by mixing 1200 parts of trypticase (Baltimore Biological Laboratories), 600 parts of yeast extract (Difco), 300 parts of maltose, 60 parts of L-cysteine hydrochloride, 12 parts of L-ascorbic acid, 48 parts of dibasic potassium phosphate, 48 parts of monobasic potassium phosphate, and 54,000 parts of distilled water. The pH is adjusted to 6.8 with 4% sodium hydroxide solution and 30 parts of agar (Baltimore Biological Laboratories) is incorporated. The mixture is boiled for one minute to dissolve the agar and it is then sterilized in an autoclave. To 80 volumes of the resultant medium is aseptically added 20 volumes of sterile Dubos medium serum. The resultant medium is inoculated with 1% (by volume) of either a 48-hour or a 72-hour culture of T. *foetus* or T. *vaginalis*, whereupon 1 mil. of the inoculated medium is mixed with 10 mg. of test compound. The mixture is incubated anaerobically at 37° C for 48 hours and then examined microscopically for the presence of motile trichomonads. If any are observed, the compound is considered inactive. If no motile trichomonads are observed, 0.1 ml. of the incubated mixture is serially diluted and mixed with additional quantities of the inoculated medium sufficient to produce concentrations of 1000, 100, 10, and 1 microgram of test compound per ml., and the resultant mixtures are incubated anaerobically as before at 37° C. for 48 hours and then examined microscopically for the presence of motile trichomonads. Controls are provided by concurrent incubations identical with the foregoing except for the absence of test compound. When N-[2-(2-methyl-5-nitro-1-imidazolyl)ethyl]succinimide, N-[2-(2-methyl-5-nitro-1-imidazolyl)ethyl]glutarimide, 3-[2-(2-methyl-5-nitro-1-imidazolyl)ethyl]-5,5-diphenylhydantoin, 3-[2-(2-methyl-5-nitro-1-imidazolyl)ethyl]-5,5-hexamethylenehydantoin, 1'-[2-(2-methyl-5-nitro-1-imidazolyl)ethyl]spiro[adamantane-2,4'-imidazoline]-2',5'-dione, N-[2-(2-methyl-5-nitro-1-imidazolyl)ethyl]naphthalimide, 3-[2-(2-methyl-5-nitro-1-imidazolyl)ethyl]-2,4-(1H,3H)-quinazolinedione, and N-[2-(2-methyl-5-nitro-1-imidazolyl)ethyl]-o-sulfobenzimide were tested against *Trichomonas vaginalis* by the above procedure, each inhibited the protozoa at a concentration of 10 micrograms per milliliter or less. Similarly, N-[2-(2-methyl-5-nitro-1-imidazolyl)ethyl]phthalimide, N-[2-(2-methyl-5-nitro-1-imidazolyl)ethyl]quinolinimide, and N-[2-(2-methyl-5-nitro-1-imidazolyl)ethyl]phthalamic acid were tested against *Tritrichomonas foetus* in the above procedure; each inhibited the protozoa at a concentration of 10 micrograms per milliliter or less.

The present compounds can be combined with various known excipients and adjuvants in the form of dusts, solutions, suspensions, ointments, and sprays to provide compositions useful for disinfecting purposes.

The following examples are presented to further illustrate the present invention; they should not be construed as limiting it in spirit or in scope. In these examples, quantities are indicated in parts by weight unless parts by volume are specified, and temperatures are indicated in degrees centigrade (° C). The relationship between parts by weight and parts by volume is the same as that existing between grams and milliliters.

EXAMPLE 1

A mixture of 17.0 parts of 1-(2-chloroethyl)-2-methyl-5-nitroimidazole, 18.0 parts of potassium phthalimide, and 2.0 parts of potassium iodide in 240 parts of dimethylformamide is heated in a boiling water bath for 3 hours with stirring. Stirring is then continued for 16 hours at room temperature. The resulting brown mixture is diluted with 870 parts of toluene and the toluene solution is washed with several portions of water. The toluene solution is dried over sodium sulfate and the solvent is evaporated to leave a residue which is digested with cold alcohol. The alcohol solution is then cooled and the precipitate which forms is separated by filtration and recrystallized from ethanol to give N-[2-(2-methyl-5-nitro-1-imidazolyl)ethyl]phthalimide melting at about 177° C. This compound has the following formula

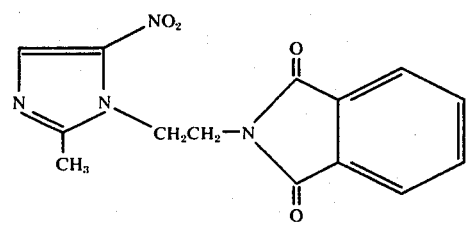

If an equivalent quantity of 1-(2-chloroethyl)-5-nitroimidazole is substituted for the 1-(2-chloroethyl)-2-methyl-5-nitroimidazole and the above procedure is repeated, the product obtained is N-[2-(5-nitro-1-imidazolyl)ethyl]phthalimide.

EXAMPLE 2

10.0 Parts of succinimide and 6.5 parts of potassium hydroxide are dissolved in 200 parts of methanol. The solvent is then evaporated under reduced pressure to leave a residual white solid. The reaction apparatus is flushed with nitrogen and dimethylformamide is added to the solid. Then, a solution of 32 parts of 1-(2-hydroxyethyl)-2-methyl-5-nitroimidazole tosylate in 145 parts of warm dimethylformamide is added and the mixture is diluted to about 300 parts by volume with dimethylformamide. The mixture is heated to 85°–102° C. with stirring for 45 minutes. The solid dissolves and the dark mixture which results is allowed to cool slowly. It is then diluted slowly with 450 parts of toluene. The precipitate which forms is allowed to digest and then an additional 450 parts of toluene is added. The precipitate is removed by filtration and washed with toluene and the toluene-dimethylformamide filtrate is heated under reduced pressure to remove the solvent. A dark residual oil is obtained and this is diluted with acetone to a volume of about 100 parts. Crystallization is then initiated and 35 parts of ether is added to the resultant mixture. The resultant precipitate is separated by filtration, washed with a mixture of acetone and ether and then with ether, and finally vacuum dried to give N-[2-(2-methyl-5-nitro-1-imidazolyl)-ethyl]succinimide melting at about 147°–148° C.

Similarly, substitution of equivalent quantities of 1-(2-hydroxyethyl)-2-ethyl-5-nitroimidazole tosylate and 1-(2-hydroxyethyl)-4-nitroimidazole tosylate for the 1-(2-hydroxyethyl)-2-methyl-5-nitroimidazole tosylate used above and substantial repetition of the procedure of this example afford, after suitable isolation, respectively, N-[2-(2-ethyl-5-nitro-1-imidazolyl)ethyl]succinimide, with a characteristic nuclear magnetic resonance band at about 475 Hz as determined in deuterochloroform, and an ultraviolet absorption maximum in methanol at about 310 µ with a molecular extinction coefficient of 8400; and N-[2-(4-nitro-1-imidazolyl)ethyl]succinimide, with a characteristic nuclear magnetic resonance band at about 160 Hz, as determined in deuterochloroform solution.

EXAMPLE 3

Naphthalimide is converted to the potassium salt and reacted with 1-(2-hydroxyethyl)-2-methyl-5-nitroimidazole tosylate according to the procedure described in Example 2. The hot solution obtained from the reaction is filtered and the precipitate which forms in the filtrate is separated by filtration and recrystallized from dimethylsulfoxide to give N-[2-(2-methyl-5-nitro-1-imidazolyl)ethyl]naphthalimide melting at about 272°–275° C.

EXAMPLE 4

A solution is prepared from 240 parts of methanol, 14 parts of 3,3-dimethylglutarimide, and 6.5 parts of potassium hydroxide. The solvent is evaporated to leave a residual syrup which is mixed with 95 parts of dimethylformamide, Then, a solution of 32 parts of 1-(2-hydroxyethyl)-2-methyl-5-nitroimidazole tosylate in 190 parts of dimethylformamide is added. The mixture becomes dark green-black immediately. It is then stirred and warmed at 90°–110° C. for about 1 hour before it is cooled and diluted slowly to a total volume of 100 parts with toluene. The precipitate which forms is removed by filtration and washed. The solvent is evaporated from the toluene-dimethylformamide filtrate under reduced pressure and the residue is dissolved in 80 parts of acetone, diluted with 280 parts of ether, mixed with charcoal, and filtered. The solvent is evaporated from the filtrate under reduced pressure and the residual oil is diluted with 140 parts of ether and made to crystallize. The precipitate which forms is separated by filtration and dried. The solid is then dissolved in an excess of warm acetone and treated with charcoal. The resulting filtrate is diluted with 35 parts of ether and crystallization is initiated. The precipitate which forms is separated by filtration, washed with ether and then with acetone. The resulting filtrate is then concentrated to a volume of 40 parts and cooled. The precipitate which forms is separated by filtration, washed, and then dried to give N-[2-(2-methyl-5-nitro-1-imidazolyl)ethyl]-3,3-dimethylglutarimide melting at about 153°–154.5° C.

EXAMPLE 5

To a solution of 5.0 parts of quinolinimide in 50 parts of dimethylformamide is added 2.0 parts of potassium hydroxide. The mixture is heated on a steam bath and 15 parts of methanol is added to dissolve the potassium hydroxide. The mixture is then diluted with 50 parts of additional dimethylformamide and the solution is heated under reduced pressure to remove the methanol. To the resulting dimethylformamide solution is added a solution of 10.0 parts of 1-(2-hydroxyethyl)-2-methyl-5-nitroimidazole tosylate in 95 parts of dimethylformamide. The resulting yellow solution is heated on a steam bath for 1 hour and the solvent is then evaporated under reduced pressure to leave a solid residue. This is triturated with 435 parts of toluene and the insoluble material is separated by filtration. The solid is mixed with 200 parts of water and the insoluble material is separated by filtration and dried to give N-[2-(2-methyl-5-nitro-1-imidazolyl)ethyl]quinolinimide melting at about 205°–213° C. This compound has the following formula

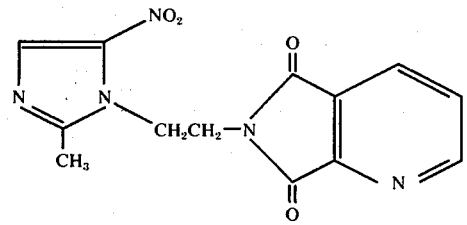

EXAMPLE 6

1.4 Parts of 1-(2-chloroethyl)-2-methyl-5-nitroimidazole is mixed with 2.5 parts of the sodium salt of 5,5-diphenylhydantoin and 75 parts of dimethylformamide is added under nitrogen. The mixture is heated on a steam bath for 1 hour and then 10 parts of methanol is added and heating is continued for an additional 4 hours. The solvent is then evaporated on the steam bath under a stream of nitrogen to leave a residual mixture of solid and oil. The residue is mixed with toluene and filtered to remove some insoluble material. The toluene solution is diluted to a volume of 250 parts and washed with a mixture of 25 parts of sodium bicarbonate and 120 parts of water. The toluene solution is then washed with water and dried over magnesium sulfate and the solvent is evaporated to leave a solid residue. This is digested in warm ether and then cooled and the solid is separated by filtration. The solid is recrystallized from ethanol to give 3-[2-(2-methyl-5-nitro-1-imidazolyl)ethyl]-5,5-diphenylhydantoin melting at about 209°–210.5° C. This compound has the following formula

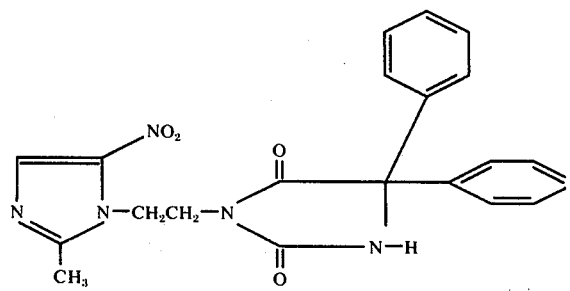

EXAMPLE 7

8.5 Parts of 1-(2-chloroethyl)-2-methyl-5-nitroimidazole is dissolved in 190 parts of dimethylformamide and 7.0 parts of the sodium salt of 5,5-dimethylhydantoin is added. The mixture is allowed to stand for about 5 hours and then filtered to remove a small amount of insoluble material. Part of the solvent is evaporated under reduced pressure and the remaining solution is diluted with toluene and filtered to remove a small amount of new insoluble material. The solvent is then evaporated from the resulting filtrate to leave a residual yellow-brown liquid. The liquid is washed twice by decantation with hexane, dissolved in ether, and treated with charcoal. The solution is then diluted with about 150 parts of benzene and the solvent is evaporated to leave a residual yellow oil. This oil is chromatographed on a silica column using benzene and eluted with solutions containing increasing quantities of ethyl acetate in benzene. After elution with 100% ethyl acetate, elution is continued with increasing quantities of ethanol in ethyl acetate. The fractions obtained by elution of the column with 10% ethanol in ethyl acetate are collected separately and combined and the solvent is evaporated to leave a residual solid. This is redissolved in methanol, and the solution is filtered, concentrated, and allowed to crystallize. The precipitate which forms is separated by filtration and then dried under vacuum at 78° C. for about 7 hours. The product obtained in this way is 3-[2-(2-methyl-5-nitro-1-imidazolyl)ethyl]-5,5-dimethylhydantoin melting at about 138°–139° C.

EXAMPLE 8

A solution is prepared from 8.5 parts of 5,5-hexamethylenehydantoin, 80 parts of hot methanol, and 95 parts of dimethylformamide. A solution of 2.9 parts of potassium hydroxide in 80 parts of methanol is added and the methanol is evaporated from the resulting solution. To the remaining dimethylformamide solution there is added a solution of 15.0 parts of 1-(2-hydroxyethyl)-2-methyl-5-nitroimidazole tosylate in 140 parts of dimethylformamide. The mixture is heated on a steam bath for 2 hours and then concentrated to about ½ the original volume. 200 Parts of water is added and the mixture is digested. The solid which forms is separated by filtration and recrystallized from methanol to give 3-[2-(2-methyl-5-nitro-1-imidazolyl)ethyl]-5,5-hexamethylenehydantoin melting at about 205°–208° C.

EXAMPLE 9

A mixture of 9.0 parts of adamantan-2-one, 5.8 parts of potassium cyanide and 19.2 parts of ammonium carbonate in 90 parts by volume of a 50% by volume ethanol-water mixture is heated in a bomb at 62° C. for 24 hours. Water is used to aid in transferring the material from the bomb and the ethanol is evaporated from the resulting mixture. The solid is separated by filtration, washed with water, dried, and then recrystallized from a mixture of water and pyridine or water, ethanol, and pyridine to give spiro[adamantane-2,4'-imidazoline]-2',5'-dione melting at about 290–293° C.

To a solution of 10 parts of spiro[adamantane-2,4'-imidazoline]-2',5'-dione in 190 parts of dimethylformamide is added a solution of 2.9 parts of potassium hydroxide in 130 parts of methanol. The methanol is removed under reduced pressure and to the remaining mixture is added a solution of 15 parts of 1-(2-hydroxyethyl)-2-methyl-5-nitroimidazole tosylate in 180 parts of dimethylformamide. The mixture is heated on a steam bath for 4 hours and then cooled and diluted with 200 parts of water. The precipitate which forms is separated by filtration and dissolved in 190 parts of dimethylformamide. This solution is diluted with 50 parts of water. The precipitate which forms is separated by filtration and digested at room temperature in 95 parts of dimethylformamide. Insoluble material is separated by filtration to give 1'-[2-(2-methyl-5-nitro-1-imidazolyl)-ethyl]spiro[adamantane-2,4'-imidazoline]-2',5'-dione melting at about 276°–280° C.

EXAMPLE 10

A mixture of 15.0 parts of 1-(2-hydroxyethyl)-2-methyl-5-nitroimidazole tosylate and 7.5 parts of 2,4(1H,–3H)-quinazolinedione is dissolved in 190 parts of warm dimethylformamide. 2.9 Parts of potassium hydroxide is dissolved in 80 parts of methanol and diluted with about 95 parts of dimethylformamide. The methanol is removed under reduced pressure, the residual solution added to the quinazolinedione solution, and the resulting mixture heated on a steam bath for 4 hours. The crude solution is cooled, filtered, and diluted with 100 parts of water. The precipitate which forms is separated by filtration and the solvent is evaporated from the filtrate to leave a residue which is stirred with 630 parts of toluene and filtered. The solvent is evaporated from the filtrate to leave a yellow residue. This is dissolved in toluene and dimethylformamide and then concentrated. A precipitate forms and it is separated by filtration to give 3-[2-(2-methyl-5-nitro-1-imidazolyl)ethyl]-2,4-(1H,3H)quinazolinedione melting at about 261°–264° C.

EXAMPLE 11

A solution of 10.0 parts of the sodium salt of o-sulfobenzimide in 95 parts of dimethylformamide is added to a solution of 9.2 parts of 1-(2-chloroethyl)-2-methyl-5-nitroimidazole in 95 parts of water. One part of sodium iodide is added and the mixture is heated at 120°–140° C. for about 90 minutes. It is then allowed to stand at room temperature for 16 hours before it is diluted with 870 parts of toluene and washed with water. The toluene solution is dried over sodium sulfate and the solvent is evaporated to leave a residual mixture of solid and syrup. The residue is then digested at room temperature with 70 parts of ether. The ether is then decanted and the solid is dried and then dissolved in chloroform. Addition of ether to the chloroform solution causes precipitation to take place. The solid which forms is separated, washed and dried. This residue is then heated with 90 parts of chloroform and filtered to remove some insoluble material. The filtrate is then concentrated and ether is added to cause precipitation. The solid which forms is separated by filtration and dried. It melts at about 176°–180° C. The product obtained in this way is N-[2-(2-methyl-5-nitro-1-imidazolyl)ethyl]-o-sulfobenzimide and it has the following formula

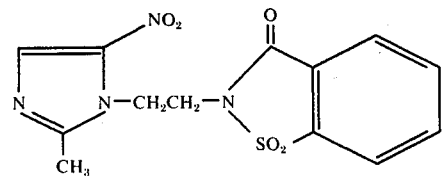

EXAMPLE 12

9.0 Parts of 4-nitrophthalimide is dissolved in 200 parts of boiling methanol. The resulting solution is cooled and a solution of 2.9 parts of potassium hydroxide in 80 parts of methanol is added. The potassium salt precipitates immediately and the liquid is removed by evaporation under reduced pressure. The resulting residue is suspended in 240 parts of dimethylformamide and a solution of 15 parts of 1-(2-hydroxyethyl)-2-methyl-5-nitroimidazole tosylate in 145 parts of dimethylformamide is added. The resulting mixture is heated on a steam bath for about 75 minutes and then concentrated to a volume of about 100 parts. The mixture is then poured onto ice and the precipitate which forms is separated by filtration. It is then crushed and dried and finally stirred and heated with about 150 parts of ethanol. The solid is again separated by filtration and dried first in the air and then overnight under reduced pressure. The resulting product is N-[2-(2-methyl-5-nitro-1-imidazolyl)ethyl]-4-nitrophthalimide melting at about 248°–250° C. with decomposition.

EXAMPLE 13

To a solution of 8.5 parts of 1,1-cyclohexanediacetimide in 120 parts of methanol is added a solution of 2.9 parts of potassium hydroxide in 80 parts of methanol and then 95 parts of dimethylformamide is added. The methanol is evaporated from the solution under reduced pressure and to the residue is added a solution of 15.0 parts of 1-(2-hydroxyethyl)-2-methyl-5-nitroimidazole tosylate in 140 parts of dimethylformamide. The mixture turns dark and is heated on a steam bath for 1 hour. It is then cooled and diluted with water to a volume of about 600 parts. The precipitate which forms is separated by filtration, washed with water, and air dried. It is then dissolved in a mixture of ethyl acetate and ether and treated with charcoal. The resulting filtrate is concentrated to a volume of about 60 parts and diluted with an equal volume of ether. The precipitate which forms is separated by filtration and recrystallized from a solution of equal volumes of ethyl acetate and ether. The product obtained in this way is N-[2-(2-methyl-5-nitro-1-imidazolyl)ethyl]-1,1-cyclohexanediacetimide melting at about 131°–133° C. This compound has the following formula

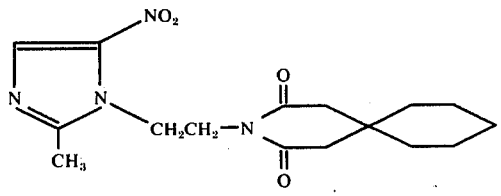

EXAMPLE 14

Glutarimide is converted to the potassium salt and reacted with 1-(2-hydroxyethyl)-2-methyl-5-nitroimidazole tosylate according to the procedure described in Example 13. The crude reaction mixture is diluted with toluene and extracted with water. The toluene solution is dried and the solvent evaporated to leave a solid residue which is digested in ether and then dried. It is then recrystallized from 2-propanol and chromatographed before a second recrystallization from 2-propanol. The product finally obtained in this way is N-[2-(2-methyl-5-nitro-1-imidazolyl)ethyl]-glutarimide melting at about 137°–139° C.

EXAMPLE 15

3-Nitrophthalimide is converted to the potassium salt by the procedure described in Example 13 and then reacted with 1-(2-chloroethyl)-2-methyl-5-nitroimidazole according to the procedure described in Example 1. The crude reaction mixture is digested with toluene and then filtered to remove some insoluble material. Evaporation of the solvent leaves a syrup which is diluted with chloroform and then filtered to remove some insoluble material. The filtrate is further diluted with toluene and again filtered to remove some precipitate. The solvent is then evaporated from the filtrate and the resulting residue is recrystallized first from ethanol and then from acetone to give N-[2-(2-methyl-5-nitro-1-imidazolyl)ethyl]-3-nitrophthalimide melting at about 175°–176° C.

EXAMPLE 16

5.5 Parts of acenaphthene-1,2-dicarboxylic acid is heated in an oil bath with an excess of concentrated ammonium hydroxide. After most of the excess of ammonium hydroxide has distilled off, the temperature of the oil bath is raised to 200° C. and it is maintained at that temperature for 45 minutes. The residual material is sublimed under vacuum (0.05–0.1 mm.) using an oil bath at 280° C. The resultant solid is recrystallized from ethanol to give acenaphthene-1,2-dicarboximide melting at about 242°–246° C.

Acenaphthene-1,2-dicarboximide is converted to the potassium salt and reacted with 1-(2-hydroxyethyl)-2-methyl-5-nitroimidazole tosylate according to the procedure described in Example 13. The crude reaction mixture is cooled and diluted with water, and then extracted with toluene. The solvent is evaporated from the toluene extract and the residue recrystallized from ethanol to give N-[2-(2-methyl-5-nitro-1-imidazolyl)ethyl]-acenaphthene-1,2-dicarboximide melting at about 183°–185° C.

EXAMPLE 17

1,2,3,6-Tetrahydrophthalimide is converted to the potassium salt and reacted with 1-(2-hydroxyethyl)-2-methyl-5-nitroimidazole tosylate according to the procedure described in Example 13. The crude reaction mixture obtained is concentrated and the concentrate distributed between water and toluene. The toluene layer is separated and the solvent is evaporated to leave a residue which is recrystallized from 2-propanol, affording N-[2-(2-methyl-5-nitro-1-imidazolyl)ethyl]-1,2,3,6-tetrahydrophthalimide melting at about 118°–123° C.

EXAMPLE 18

A solution of 8 parts of potassium hydroxide pellets in 80 parts of warm methanol is added to a warm solution of 20 parts of cyclohexane-1,2-dicarboximide in dimethylformamide. The mixture is diluted with about 160 parts of 2-propanol and then concentrated under reduced pressure to a volume of about 100 parts. This solution is divided into two equal portions and, to one portion, there is added a solution of 16.2 parts of 1-(2-hydroxyethyl)-2-methyl-5-nitroimidazole methylsulfonate in 95 parts of hot dimethylformamide. The mixture darkens and is heated on a steam bath for 16 minutes and then allowed to cool for 30 minutes. The resulting mixture is diluted with cold water to a volume of 500 parts. It is then extracted twice with toluene and the combined toluene extracts are washed once with water and dried over sodium sulfate and the solvent is evaporated under reduced pressure to leave an orange-yellow syrup which crystallizes slowly. This is digested at room temperature with about 50 parts of 2-propanol and the insoluble crystalline material is separated by filtration, washed, and dried. The product thus obtained is N-[2-(2-methyl-5-nitro-1-imidazolyl)ethyl]-cyclohexane-1,2-dicarboximide melting at about 88°–90° C.

EXAMPLE 19

To a mixture of 5.0 parts of N-[2-(2-methyl-5-nitro-1-imidazolyl)ethyl]phthalimide and 80 parts of methanol is added 7.6 parts by volume of a 2.5 N aqueous sodium hydroxide solution and the mixture is stirred at room temperature. Most of the imide dissolves after about 15 minutes but stirring is continued for an additional 3 hours. The reaction mixture is then diluted with 50 parts of ether, benzene is added, and the solvent is evaporated under reduced pressure. The residual dark oil is taken up in water and acidified with acetic acid. Evaporation of the solvent is again carried out although it is stopped briefly to remove some dark precipitate. On continued evaporation, a crystalline precipitate forms. This is separated by filtration, washed and dried. This solid is then mixed with water and 15 parts by volume of 1N sodium hydroxide solution under nitrogen. It dissolves slowly to give a dark solution which is filtered to remove some insoluble material. The filtrate is neutralized with dilute acetic acid to give a light orange solution from which a fine powder precipitates. The solid which forms is separated by filtration and the filtrate is acidified with acetic acid. The crystalline precipitate which forms is separated by filtration, washed, and dried in a vacuum. It decomposes at 182°–183° C. The product obtained in this way is N-[2-(2-methyl-5-nitro-1-imidazolyl)ethyl]phthalamic acid and it has the following formula

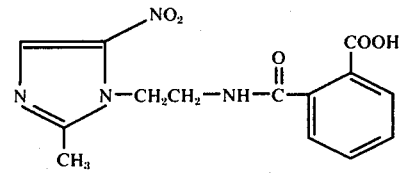

EXAMPLE 20

A suspension of 200 parts of 1-(2-hydroxyethyl)-2-methyl-5-nitroimidazole in 600 parts of pyridine is cooled to 5° C. in an ice bath and 140 parts of methanesulfonyl chloride is added portionwise at 0°–5° C. over a period of 4 hours. The mixture is then stirred at about 0° C. for 1 hour before it is slowly diluted with 600 parts of water while maintaining the temperature at 0°–5° C. The solid which forms is separated by filtration, washed with water and dried to give 1-(2-hydroxyethyl)-2-methyl-5-nitroimidazole methylsulfonate. Tosylates of 1-(2-hydroxyethyl)imidazoles are prepared in a similar manner using p-toluenesulfonyl chloride.

What is claimed is:

1. A compound which is N-[2-(2-methyl-5-nitro-1-imidazolyl)ethyl]naphthalimide.

* * * * *